US008629296B2

(12) United States Patent
Qi et al.

(10) Patent No.: US 8,629,296 B2
(45) Date of Patent: Jan. 14, 2014

(54) PYRETHROID COMPOUND, PREPARATION PROCESS AND USE THEREOF

(75) Inventors: Mingzhu Qi, Jiangsu (CN); Jingmei Zhou, Jiangsu (CN); Youfa Jiang, Jiangsu (CN); Shuze He, Jiangsu (CN)

(73) Assignees: Jiangsu Yangnong Chemical Co., Ltd., Yangzhou, Jiangsu (CN); Youth Chemical Co., Ltd., Yangzhou, Jiangsu (CN)

( * ) Notice: Subject to any disclaimer, the term of this patent is extended or adjusted under 35 U.S.C. 154(b) by 0 days.

(21) Appl. No.: 13/259,275

(22) PCT Filed: Feb. 11, 2010

(86) PCT No.: PCT/CN2010/070669
§ 371 (c)(1),
(2), (4) Date: Sep. 23, 2011

(87) PCT Pub. No.: WO2010/133098
PCT Pub. Date: Nov. 25, 2010

(65) Prior Publication Data

US 2012/0076846 A1 Mar. 29, 2012

(30) Foreign Application Priority Data

May 21, 2009 (CN) .......................... 2009 1 0143250
Jun. 5, 2009 (CN) .......................... 2009 1 0142185
Jun. 5, 2009 (CN) .......................... 2009 1 0142187

(51) Int. Cl.
*C07C 69/747* (2006.01)

(52) U.S. Cl.
USPC .......................................................... 560/124

(58) Field of Classification Search
None
See application file for complete search history.

(56) References Cited

FOREIGN PATENT DOCUMENTS

| | | |
|---|---|---|
| CN | 101381306 A | 3/2009 |
| CN | 101632377 | 1/2010 |
| CN | 101671251 A | 3/2010 |
| JP | 2002145828 | 5/2002 |

OTHER PUBLICATIONS

JP2002145828A Machine translation.*
International Search Report in International Application No. PCT/CN2010/070669, dated May 13, 2010.

* cited by examiner

*Primary Examiner* — Yevegeny Valenrod
(74) *Attorney, Agent, or Firm* — Marshall, Gerstein & Borun LLP

(57) ABSTRACT

Disclosed are a pyrethroid compound, a preparation process and the use thereof, wherein the compound is a stereoisomer of 2,3,5,6-tetrafluoro-4-methoxymethylbenzyl-3-(3,3,3-trifluoro-1-propenyl)-2,2-dimethylcyclopropanecarboxylate. The structure of the compound is represented by formula (A), in which the carbon-carbon double bond in carboxylic acid section is Z configuration, and the absolute stereo configuration at the 1-position of cyclopropane is R, namely, the said compound is 2,3,5,6-tetrafluoro-4-methoxymethylbenzyl-1R-(Z)-3-(3,3,3-trifluoro-1-propenyl)-2,2-dimethylcyclopropanecarboxylate. The said pyrethroid compound has a high activity, and has a significant effect on preventing and curing sanitary pests.

(A)

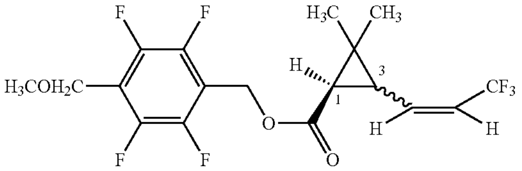

13 Claims, No Drawings

PYRETHROID COMPOUND, PREPARATION PROCESS AND USE THEREOF

CROSS-REFERENCE TO RELATED APPLICATIONS

This is the U.S. national phase of International Application No. PCT/CN2010/070669, filed Feb. 11, 2010, which claims the benefit of Chinese Patent Application No. 200910143250.X, filed May 21, 2009, Chinese Patent Application No. 200910142185.9, filed Jun. 5, 2009, and Chinese Patent Application No. 200910142187.8, filed Jun. 5, 2009.

TECHNICAL FIELD

The present invention relates to a pyrethroid compound, preparation process and use in controlling sanitary pests thereof.

BACKGROUND ART

It is well known that pyrethroid compounds can be used to control mosquitoes and insects, and have a high pesticidal activity. They have been widely used in the field of sanitary pests control due to their outstanding properties, such as high efficiency, low toxicity and residue, and good environmental compatibility. However, mosquitoes have obtained certain resistance against some traditional pyrethroid products (for example, allethrin)(Gao Xiwu et al, Chinese Journal of Vector Biology and Control, 2004, 15 (2), 105), the additive amount of pyrethroid in mosquito-repellent incense or aerosol required to achieve the same effect in controlling sanitary pests as before is increased. Therefore, not only production cost is increased but also the burden of environment is aggravated.

CN 101381306A discloses a series of novel fluoro-containing pyrethroid compounds formed by structural transformation of acid and/or alcohol moieties in traditional pyrethroids. Preliminary efficiency tests on these compounds show that these compounds have good pesticidal activity, quick knock-down and high fatality rate. On the other hand, with the growing demanding for environment protection, people pay more attention to pesticides with high biological activity. Pyrethroids usually have many optical isomers, and the biological activity of each isomer is quite different, so the study on preparation of highly active isomer is necessary. In respect to environmental protection, the use of highly active isomer can reduce the amount of pesticides without reducing pesticide effect, therefore reducing the toxicity toward non-targeted organisms and improving safety, lessening environmental pollution of pesticide residue. Based on such an idea, we made a deep investigation on 2,3,5,6-tetrafluoro-4-methoxymethylbenzyl-3-(3,3,3-trifluoro-1-propenyl)-2,2-dimeth ylcyclopropane carboxylate with a good activity, the cyclopropane moiety of the compound has two asymmetric carbon atoms and therefore isomers exist, and the carboxylic acid moiety of the compound contains a carbon-carbon double bond and therefore Z and E isomers exist. We have found through experiments that the compound with an absolute stereochemistry of cyclopropane-1 of R configuration has higher efficacy than the compound with S configuration; the compound with carbon-carbon double bond of carboxylic acid moiety of Z configuration has better efficacy than the compound with E configuration of compounds, which proved that the 2,3,5,6-tetrafluoro-4-methoxymethylbenzyl-1R-(Z)-3-(3,3,3-trifluoro-1-propenyl)-2,2-dimethylcyclopropanecarboxylate is a highly active isomer. Using this compound to control sanitary pests doesn't have cross resistance as compared to prior traditional pyrethroid products such as allethrin, and greatly reduces the dosage and the use-cost, and therefore lessens the burden on the environment due to its high basic activity.

SUMMARY OF THE INVENTION

The primary object of the present invention is to provide a pyrethroid compound with high activity and a better effect on controlling of sanitary pests.

The present invention also provides a preparation process and an use in the field of pests control of said pyrethroid compound.

The object of the present invention is achieved through the following technical solutions.

Provided is a pyrethroid compound, which is a stereoisomer of 2,3,5,6-tetrafluoro-4-methoxymethylbenzyl-3-(3,3,3-trifluoro-1-propenyl)-2,2-dimeth ylcyclopropanecarboxylate, the structure of the compound is represented by formula (A)

(A)

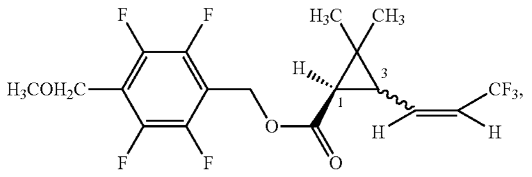

wherein the carbon-carbon double bond in carboxylic acid moiety is Z configuration, and the absolute stereo configuration at the 1-position of cyclopropane is R configuration, namely, the compound is 2,3,5,6-tetrafluoro-4-methoxymethyl benzyl-1R-(Z)-3-(3,3,3-trifluoro-1-propenyl)-2,2-dimethylcyclopropanecarboxylate.

The pyrethroid compound of formula (A) above has cis and trans isomers due to the asymmetry of cyclopropane plane. Therefore, the pyrethroid compound can be one of cis and trans isomers (it can be 2,3,5,6-tetrafluoro-4-methoxymethylbenzyl-1R, trans-(Z)-3-(3,3,3-trifluoro-1-propenyl)-2,2-dimethylcyclopropanecarboxylate, it can also be 2,3,5,6-tetrafluoro-4-methoxymethylbenzyl-1R, cis-(Z)-3-(3,3,3-trifluoro-1-propenyl)-2,2-dimethylcyclopropanecarboxylate), or mixture of both isomers mixed in any proportion. The efficacy difference caused by such an isomerism is not significant, and our study showed that the efficacy of the trans isomer was slightly better than the cis isomer.

A synthesis process of the pyrethroid compound is as follows. An esterification reaction between 1R-(Z)-3-(3,3,3-trifluoro-1-propenyl)-2,2-dimethylcyclopropane carboxylic acid represented by formula (B)

(B)

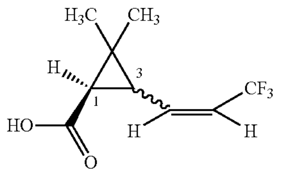

and 2,3,5,6-tetrafluoro-4-methoxymethylbenzyl alcohol is performed at a molar ratio of 0.8~1.2:1 in the presence of sulfuric acid or p-toluenesulfonic acid in an organic solvent at 60-130° C., wherein the molar ratio of catalyst sulfuric acid or p-toluenesulfonic acid to 2,3,5,6-tetrafluoro-4-methoxymethylbenzyl alcohol is 0.01~0.1:1.

Another synthesis process of the pyrethroid compound is as follows. 1R-(Z)-3-(3,3,3-trifluoro-1-propenyl)-2,2-dimethylcyclopropane carboxylic acid represented by formula (B) is acyl chloridized by a acyl chloridizing reagent to obtain 1R-(Z)-3-(3,3,3-trifluoro-1-propenyl)-2,2-dimethylcyclopropane carboxylic acid chloride, followed by reacting with 2,3,5,6-tetrafluoro-4-methoxymethyl benzyl alcohol, wherein the acyl chloridizing reagent can be thionyl chloride.

The 1R-(Z)-3-(3,3,3-trifluoro-1-propenyl)-2,2-dimethylcyclopropane carboxylic acid of formula (B) can be synthesized by a variety of processes among available techniques. Preferably, it is obtained by isolating 1R-3-(3,3,3-trifluoro-1-propenyl)-2,2-dimethylcyclopropane carboxylic acid by recrystallization, wherein the solvent used for recrystallization is methanol-water, the weight ratio of methanol to water is 0.1~10:1 and that of 1R-3-(3,3,3-trifluoro-1-propenyl)-2,2-dimethyl cyclopropane carboxylic acid to the solvent used for recrystallization is 0.05~0.1:1.

The 1R-3-(3,3,3-trifluoro-1-propenyl)-2,2-dimethyl-cyclopropane carboxylic acid can be synthesized by a variety of processes among available techniques. Preferably, it is obtained by reacting an aldehyde ester of formula (C)

(C)

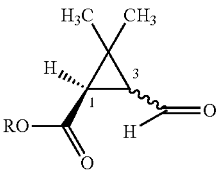

wherein R=$CH_3$, $CH_2CH_3$ with a wittig reagent $(C_6H_5)_3P^+—CH_2CF_3—$ at a molar ratio of 0.8~1.2:1 in THF under 0-40° C. for 5~20 hours to form a compound of formula (D)

(D)

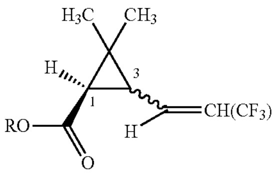

wherein R=$CH_3$, $CH_2CH_3$, followed by hydrolysis.

The compound of formula (D) can be hydrolyzed in dilute acid or alkaline solution and then the hydrolyzed product is acidized with an inorganic acid such as sulfuric acid to obtain 1R-3-(3,3,3-trifluoro-1-propenyl)-2,2-dimethylcyclopropane carboxylic acid.

The present invention also provides a use of the pyrethroid compound of formula (A) in controlling sanitary pests, such as mosquitoes, flies or blattella germanicas.

Said use is characterized in that a variety of pesticide containing the pyrethroid compound of formula (A) as an active pharmaceutical ingredient is prepared to control mosquitoes, flies or blattella germanicas.

Since the pyrethroid compound according to the present invention has a higher vapour pressure compared to traditional pyrethroid compounds, therefore, a variety of pesticides, such as pesticide incense coil, electric heating mosquito-repellent mat or electric heating liquid mosquito-repellent incense containing the compound can be prepared, the compound is volatilizable under heating; or a ribbon-shaped paper containing the compound can be prepared, the compound is volatilizable at room temperature.

EXAMPLES

The technical solutions and effects of the present invention will be illustrated with reference to the following examples. It should be understand that the present invention is not limited to these examples.

Preparation Example 1

Preparation of 1R-3-(3,3,3-trifluoro-1-propenyl)-2,2-dimethylcyclopropane carboxylic acid with cis-trans ratio of 1:1

To a 250 ml four-neck flask were added 1R-methyl 3-aldehydro-2,2-dimethylcyclopropane carboxylate with cis-trans ratio of 1:1 (15.6 g, 0.1 mol) and anhydrous tetrahydrofuran (50 ml), and followed by potassium tert-butanol (0.5 g). To the mixture was added dropwise a suspension of $(C_6H_5)_3P^+—CH_2CF_3^-$ (34.5 g, 0.1 mol) in tetrahydrofuran (80 ml) with stirring under 5° C. in 2 hrs, then the resulting mixture was heated to 20° C. and kept at this temperature for 8 hrs. THF was removed under vacuum (50 mmHg), and then toluene (100 ml) was added. The mixture was washed with water (200 m1×2), and the toluene layer was separated. Sodium hydroxide solution (100 g, 10%) was added and then heated to 80° C. with stirring for 2 hrs. The mixture was allowed to cool to room temperature and the toluene layer was separated. The water layer was transferred to a 250 ml three-neck flask in the ice-water bath and a sulfuric acid solution (30%, 100 g) was added, keeping the temperature below 5° C. A volume of flocculent precipitate in off-white precipitated and was filtered, washed with water (20 m1×2) and air-dried, then heated under vacuum to 100° C. to remove solvent toluene and obtain 1R-3-(3,3,3-trifluoro-1-propenyl)-2,2-dimethylcyclopropane carboxylic acid with cis-trans ratio of 1:1 (16.4 g; content: 92.3%; yield: 72.7%).

Preparation Example 2

Preparation of 1R-(Z)-3-(3,3,3-trifluoro-1-propenyl)-2,2-dimethylcyclopropane carboxylic acid with cis-trans ratio of 1:1

To a 100 ml beaker was added 1R-3-(3,3,3-trifluoro-1-propenyl)-2,2-dimethyl cyclopropane carboxylic acid with cis-trans ratio of 1:1 from preparation example 1 (16.4 g, 92.3%) and followed by methanol-water solution (1:1 by weight, 30 g). The resulting mixture was stirred at 40° C. for 30 mins and then filtered. The resulting solid was added into methanol-water solution (1:2 by weight, 15 g) and stirred 30 mins at 30° C., then filtered again. The resulting solid was washed with water (5 ml) and air-dried to obtain 1R-(Z)-3-(3,3,3-trifluoro-1-propenyl)-2,2-dimethylcyclopropane carboxylic acid with cis-trans ratio of 1:1 (5.8 g, content: 98.7%). The mother liquors from twice filtrations were combined and concentrated under vacuum (100 mmHg) at 40° C. in a thin film evaporator till solid precipitated. The concentrated liquid was cooled to 5° C., some solid precipitated, and then was filtrated and air-dried to obtain 1R-(Z)-3-(3,3,3-trifluoro-1- propenyl)-2,2-dimethylcyclopropane carboxylic acid with cis-trans ratio of 1:1 (4.2 g; content:95.1%).

Preparation Example 3

Preparation of 2,3,5,6-tetrafluoro-4-methoxymethyl benzyl-1R-(Z)-3-(3,3,3-trifluoro-1-propenyl)-2,2-dimethylcyclopropane carboxylate at cis-trans ratio of 1:1 (Compound 1)

To a 500 ml flask were added 1R-(Z)-3-(3,3,3-trifluoro-1-propenyl)-2,2-dimethylcyclopropane carboxylic acid with cis-trans ratio of 1:1 (20.8 g, 0.1 mol, prepared as described in preparation example 2) and 2,3,5,6-tetrafluoro-4-methoxymethylbenzyl alcohol (22.4 g, 0.1 mol) and toluene (180 ml), and then a water separator was installed to the flask. To the mixture was added p-toluenesulfonic acid (0.1 g) and heated to reflux. The reaction is carried out in absence of water for 6 hrs, during which toluene (20 ml) was added, and then the reaction was cooled to room temperature, washed with water (once, 100 g), dilute hydrochloric acid (once, 100 g, 5%), sodium bicarbonate solution (once, 100 g, 5%), and finally water (once, 100 g). The toluene layer was collected and heated under vacuum (10 mmHg) to 100° C. to remove solvent toluene and obtain 2,3,5,6-tetrafluoro-4-methoxymethylbenzyl-1R-(Z)-3-(3,3,3-trifluoro-1-propenyl)-2,2-dimethylcyclopropane carboxylate (compound 1, 36.9 g; content: 98.3%; yield:90.7%; cis-trans ratio:1:1). The molecular formula of the compound is $C_{18}H_{17}F_7O_3$ (molecular weight: 414), $^1$H NMR ($^1$H (ppm) $CDCl_3$) 1.29 (m, 6H); 1.69 (d, 1H); 2.44 (m, 1H); 3.40 (s, 3H); 4.59 (s, 2H); 5.30 (s, 2H); 5.60 (m, 1H); 5.80 (m, 1H), optical rotation α=+37.2°.

Preparation Example 4

Preparation of control compound 2,3,5,6-tetrafluoro-4-methoxymethylbenzyl-1R-(E)-3-(3,3,3-trifluoro-1-propenyl)-2,2-dimethyl cyclopropane carboxylate with cis-trans ratio of 1:1 (compound 2)

According to the process as described in preparation example 3, 1R-(E)-3-(3,3,3-trifluoro-1-propenyl)-2,2-dimethylcyclopropane carboxylic acid with cis-trans ratio of 1:1 (20.8 g, 0.1 mol) was reacted with 2,3,5,6-tetrafluoro-4-methoxymethylbenzyl alcohol (22.4 g, 0.1 mol) to obtain 2,3,5,6-tetrafluoro-4-methoxymethylbenzyl-1R-(E)-3-(3,3,3-trifluoro-1-propenyl)-2,2-dimethylcyclopropane carboxylate (compound 2, 35.8 g; content: 97.9%). The molecular formula of the compound is $C_{18}H_{17}F_7O_3$ (molecular weight: 414), $^1$H NMR ($^1$H (ppm) $CDCl_3$) 1.29 (m, 6H); 1.71 (d, 1H); 2.12 (m, 1H); 3.41 (s, 3H); 4.59 (s, 2H); 5.27 (m, 2H); 5.79 (m, 1H); 6.03 (m, 1H), optical rotation α=+37.2°.

Preparation Example 5

Preparation of control compounds 2,3,5,6-tetrafluoro-4-methoxymethylbenzyl-1S-(Z)-3-(3,3,3-trifluoro-1-propenyl)-2,2-dimethyl cyclopropane carboxylate with cis-trans ratio of 1:1 (compound 3) and 2,3,5,6-tetrafluoro-4-methoxymethylbenzyl-1S-(E)-3-(3,3,3-trifluoro-1-propenyl)-2,2-dimethylcyclopropane carboxylate with cis-trans ratio of 1:1 (Compound 4)

1S-3-(3,3,3-trifluoro-1-propenyl)-2,2-dimethylcyclopropane carboxylic acid with cis-trans ratio of 1:1 can be obtained by using 1S-methyl 3-aldehydro-2,2-dimethylcyclopropane carboxylate with cis-trans ratio of 1:1 as starting material according to the process as described in preparation example 1. Then the obtained product was recrystallized to get 15-(Z)-3-(3,3,3-trifluoro-1-propenyl)-2,2-dimethylcyclopropane carboxylic acid and 1S-(E)-3-(3,3,3-trifluoro-1-propenyl)-2,2-dimethylcyclopropane carboxylic acid according to the process as described in preparation example 2.

According to the process as described in preparation example 3,1S-(Z)-3-(3,3,3-trifluoro-1-propenyl)-2,2-dimethylcyclopropane carboxylic acid was reacted with 2,3,5,6-tetrafluoro-4-methoxymethylbenzyl alcohol to obtain 2,3,5,6-tetrafluoro-4-methoxymethylbenzyl-1S-(Z)-3-(3,3,3-trifluoro-1-propenyl)-2,2-dimethylcyclopropane carboxylate (compound 3), wherein the ratio of 2,3,5,6-tetrafluoro-4-methoxymethylbenzyl-1S, cis-(Z)-3-(3,3,3-trifluoro-1-propenyl)-2,2-dim ethylcyclopropane carboxylate to 2,3,5,6-tetrafluoro-4-methoxymethylbenzyl-1S, trans-(Z)-3-(3,3,3-trifluoro-1-propenyl)-2,2-dimethylcyclopropane carboxylate is 1:1). The molecular formula of the compound is $C_{18}H_{17}F_7O_3$ (molecular weight: 414), $^1$H NMR ($^1$H (ppm) $CDCl_3$) 1.29 (m, 6H); 1.69 (d, 1H); 2.44 (m, 1H); 3.40 (s, 3H); 4.59 (s, 2H); 5.30 (s, 2H); 5.60 (m, 1H); 5.80 (m, 1H), optical rotation α=−37.2°.

1S-(E)-3-(3,3,3-trifluoro-1-propenyl)-2,2-dimethyl-cyclopropane carboxylic acid with cis-trans ratio of 1:1 was reacted with 2,3,5,6-tetrafluoro-4-methoxymethylbenzyl alcohol to obtain 2,3,5,6-tetrafluoro-4-methoxymethylbenzyl-1S-(E)-3-(3,3,3-trifluoro-1-propenyl)-2,2-dimethylcyclopropane carboxylate (compound 4), wherein the ratio of 2,3,5,6-tetrafluoro-4-methoxymethylbenzyl-1S, cis-(E)-3-(3,3,3-trifluoro-1-propenyl)-2,2-dimethylcyclopropane carboxylate to 2,3,5,6-tetrafluoro-4-methoxymethylbenzyl-1S, trans-(E)-3-(3,3,3-trifluoro-1-propenyl)-2,2-dimethylcyclopropane carboxylate is 1:1). The molecular formula of the compound is $C_{18}H_{17}F_7O_3$ (molecular weight: 414), $^1$H NMR ($^1$H (ppm) $CDCl_3$) 1.29 (m, 6H); 1.71 (d, 1H); 2.12 (m, 1H); 3.41 (s, 3H); 4.59 (s, 2H); 5.27 (m, 2H); 5.79 (m, 1H); 6.03 (m, 1H), optical rotation α=−37.2°.

Preparation Example 6

Preparation of 2,3,5,6-tetrafluoro-4-methoxymethyl benzyl-1R, cis-(Z)-3-(3,3,3-trifluoro-1-propenyl)-2,2-dimethyl-cyclopropane carboxylate (Compound 5)

According to the process as described in preparation example 3, 1R, cis-(Z)-3-(3,3,3-trifluoro-1-propenyl)-2,2-dimethylcyclopropane carboxylic acid (20.8 g, 0.1 mol) was reacted with 2,3,5,6-tetrafluoro-4-methoxymethylbenzyl alcohol (22.4 g, 0.1 mol) to obtain 2,3,5,6-tetrafluoro-4-methoxymethylbenzyl-1R, cis-(Z)-3-(3,3,3-trifluoro-1-propenyl)-2,2-dimethyl-cyclopropane carboxylate (compound 5, 34.9 g; content: 98.2%). The molecular formula of the compound is $C_{18}H_{17}F_7O_3$ (molecular weight: 414), $^1$H NMR ($^1$H (ppm) $CDCl_3$) 1.29 (m, 6H); 1.69 (d, 1H); 2.44 (m, 1H); 3.40 (s, 3H); 4.59 (s, 2H); 5.30 (s, 2H); 5.60 (m, 1H); 5.80 (m, 1H), coupling constant of two H atoms on cyclopropane plane 3J=8.9 Hz, optical rotation α=+37.2°.

Preparation Example 7

Preparation of 2,3,5,6-tetrafluoro-4-methoxymethyl benzyl-1R, trans-(Z)-3-(3,3,3-trifluoro-1-propenyl)-2,2-dimethylcyclopropane carboxylate (compound 6)

According to the process as described in preparation example 3, 1R, trans-(Z)-3-(3,3,3-trifluoro-1-propenyl)-2,2- dimethylcyclopropane carboxylic acid (20.8 g, 0.1 mol) was reacted with 2,3,5,6-tetrafluoro-4-methoxymethylbenzyl alcohol (22.4 g, 0.1 mol) to obtain 2,3,5,6-tetrafluoro-4-methoxymethylbenzyl-1R, trans-(Z)-3-(3,3,3-trifluoro-1-propenyl)-2,2-dimethyl cyclopropane carboxylate (compound 6, 35.2 g, content: 98.0%). The molecular formula of the compound is $C_{18}H_{17}F_7O_3$ (molecular weight: 414), $^1H$ NMR ($^1H$ (ppm) $CDCl_3$) 1.29 (m, 6H); 1.69 (d, 1H); 2.44 (m, 1H); 3.40 (s, 3H); 4.59 (s, 2H); 5.30 (s, 2H); 5.60 (m, 1H); 5.80 (m, 1H), coupling constant of two H atoms on cyclopropane plane 3J=5.4 Hz, optical rotation α=+37.2°.

Preparation Example 8

Preparation of 2,3,5,6-tetrafluoro-4-methoxymethyl benzyl-1R-(Z)-3-(3,3,3-trifluoro-1-propenyl)-2,2-dimethylcyclopropane carboxylate with cis-trans ratio of 1:9 (Compound 7)

According to the process as described in preparation example 3, 1R,-(Z)-3-(3,3,3-trifluoro-1-propenyl)-2,2-dimethylcyclopropane carboxylic acid (20.8 g, 0.1 mol, prepared from 1R-methyl 3-aldehydeo-2,2-dimethylcyclopropane carboxylate with cis-trans ratio of 1:9 as starting material) was reacted with 2,3,5,6-tetrafluoro-4-methoxymethylbenzyl alcohol (22.4 g, 0.1 mol) to obtain 2,3,5,6-tetrafluoro-4-methoxymethylbenzyl-1R-(Z)-3-(3,3,3-trifluoro-1-propenyl)-2,2-dimethylcyclopropane carboxylate with cis-trans ratio of 1:9 (compound 7, 33.6 g; content: 98.2%). The molecular formula of the compound is $C_{18}H_{17}F_7O_3$ (molecular weight: 414), $^1H$ NMR ($^1H$ (ppm) $CDCl_3$) 1.29 (m, 6H); 1.69 (d, 1H); 2.44 (m, 1H); 3.40 (s, 3H); 4.59 (s, 2H); 5.30 (s, 2H); 5.60 (m, 1H); 5.80 (m, 1H), optical rotation α=+37.2°.

Preparation Example 9

Preparation of 2,3,5,6-tetrafluoro-4-methoxy methylbenzyl-1R-(Z)-3-(3,3,3-trifluoro-1-propenyl)-2,2-dimethylcyclopropane carboxylate with cis-trans ratio of 2:8 (compound 8)

According to the process as described in preparation example 3, 1R-(Z)-3-(3,3,3-trifluoro-1-propenyl)-2,2-dimethylcyclopropane carboxylic acid with cis-trans ratio of 2:8 (20.8 g, 0.1 mol, prepared from 1R-methyl 3-aldehydro-2,2-dimethylcyclopropane carboxylate with cis-trans ratio of 2:8 as starting material) was reacted with 2,3,5,6-tetrafluoro-4-methoxymethylbenzyl alcohol (22.4 g, 0.1 mol) to obtain 2,3,5,6-tetrafluoro-4-methoxymethylbenzyl-1R-(Z)-3-(3,3,3-trifluoro-1-propenyl)-2,2-dimethylcyclopropane carboxylate with cis-trans ratio of 2:8 (compound 8, 34.1 g, content: 98.4%). The molecular formula of the compound is $C_{18}H_{17}F_7O_3$ (molecular weight: 414), $^1H$ NMR ($^1H$ (ppm) $CDCl_3$) 1.29 (m, 6H); 1.69 (d, 1H); 2.44 (m, 1H); 3.40 (s, 3H); 4.59 (s, 2H); 5.30 (s, 2H); 5.60 (m, 1H); 5.80 (m, 1H), optical rotation α=+37.2°.

Use Example 1

To a mixture of corn starch, carbon powder and wood flour (1:5:4, 99.96 parts by weight) was added water (120 parts by weight) and the resulting mixture was kneaded, and then dried to give a pesticide incense coil substrate (diameter: 12.0 cm; thickness: 4 mm; one pair of substrates' weight: 40 g).

On the other hand, a 0.4 w/v % solution of compound 1 in kerosene was prepared.

The above solution (4 ml) was uniformly sprayed on the incense coil substrate with a micro-syringe, and then kept for airing at room temperature for 3 hours to get of a pesticide incense coil I containing compound 1 according to the present invention (0.04 w/w %).

Similarly, a 0.4 w/v % solution of compound 2 in kerosene was prepared and a pesticide incense coil II containing compound 2 (0.04 w/w %) was be obtained.

A 0.4 w/v % solution of compound 3 in kerosene was prepared and a pesticide incense coil III containing compound 3 (0.04 w/w %) was obtained;

A 0.4 w/v % solution of compound 4 in kerosene was prepared and a pesticide incense coil IV containing compound 4 (0.04 w/w %) was obtained;

A 0.4 w/v % solution of compound 6 in kerosene was prepared and a pesticide incense coil V containing compound 6 (0.04 w/w %) was obtained;

A 0.4 w/v % solution of dimefluthrin in kerosene was prepared and a pesticide incense coil VI containing dimefluthrin (0.04 w/w %) was obtained.

The efficacy of pesticide coils I-Vi on mosquito were tested and compared according to GB13917.4-92). In particular, the test pests are female Culex pipiens pallens (2-3 days old, fasten). Firstly, 20 test mosquitoes were captured and put into airtight cask testing device with a mosquito-sucking tube, a section of pesticide incense coil to be tested was put on shelves, then ignited and removed after 1 min. Finally, the number of killed mosquito is recorded at regular intervals, and the results were showed in table 1:

TABLE 1 comparison of efficacy of the compounds according to the present invention and control compound on mosquito

| Pesticide incense coil | Active ingredient | Concentration w/w % | KT50 (min) |
|---|---|---|---|
| Pesticide incense coil I | Compound 1 | 0.04 | 3.2 |
| Pesticide incense coil II | Compound 2 | 0.04 | 5.2 |
| Pesticide incense coil III | Compound 3 | 0.04 | 5.1 |
| Pesticide incense coil IV | Compound 4 | 0.04 | 8.2 |
| Pesticide incense coil V | Compound 6 | 0.04 | 3.1 |
| Pesticide incense coil VI | Dimefluthrin | 0.04 | 7.6 |

The results showed that the relative efficacy of both compound 1 (2,3,5,6-tetrafluoro-4-methoxymethylbenzyl-1R-(Z)-3-(3,3,3-trifluoro-1-propenyl)-2,2-dimethylcyclopropane carboxylate with cis-trans ratio of 1:1 of) and compound 6 (2,3,5,6-tetrafluoro-4-methoxymethylbenzyl-1R, trans-(Z)-3-(3,3,3-trifluoro-1-propen yl)-2,2-dimethylcyclopropane carboxylate) with 1R, Z configuration according to the present invention are more than twice that of dimefluthrin, and substantially superior to that of compounds 2, 3 and 4.

Use Example 2

Compound 1 (0.3 parts by weight) and kerosene (59.7 parts by weight) are mixed under heating to prepare a pesticide. The pesticide was placed in aerosol cans with a valve and then a mixture of propane and butane (40.0 parts by weight) was injected into tank through the valve at positive pressure to get an aerosol pesticide, which contains 10.3 w/w % compound 1.

The efficacy of the aerosol pesticide on Mosquitoes, flies and blattella germanicas were tested according to GB13917.2-92. In particular, the test pests were placed into a tank. After all test pests restored normal activities, 1 g aerosol pesticide from aerosol cans was sprayed into the tank. Take the barrier plate away to make pests exposed to the aerosol pesticide and the number of killed pests was recorded at regular intervals, then all test pests were transferred to a clean cage after 20 mins, the number of dead pests was counted after 24 hours and the mortality of blattella germanicas at 72 h was determined. The results were showed in table 2:

TABLE 2

The efficacy of aerosol pesticide made from the compound according to the present invention on mosquito, fly and *blattella germanicas*

| Pest | KT50 (mosquito/fly/cockroach) | Mortality during 24 h |
|---|---|---|
| Mosquito | 4.8 min | 100% |
| Fly | 4.3 min | 100% |
| *Blattella germanica* | 6.2 min | 90% (72 h) |

The results showed that the aerosol pesticide made from compound 1 according to the present invention has excellent efficacy on mosquitoes, flies and blattella germanicas.

Use Example 3

Compound 6 (2,3,5,6-tetrafluoro-4-methoxymethylbenzyl-1R, trans-(Z)-3-(3,3,3-trifluoro-1-prop ylene)-2,2-dimethylcyclopropane carboxylate, 1 mg) was dissolved in acetone (20 ml) to obtain a solution. The resulting solution was distributed on a filter paper (20 cm×50 cm) and air-dried to remove the acetone to obtain a volatile agent. None mosquito invaded when the as-obtained volatile agent was hung on the edge of the door of a room.

What is claimed is:

1. A pesticide comprising a pyrethroid compound, which is a stereoisomer of 2,3,5,6-tetrafluoro-4-methoxymethylbenzyl-3-(3,3,3-trifluoro-1-propenyl)-2,2-dimethylcyclopropanecarboxylate, characterized in that the structure of the compound is represented by formula (A)

(A)

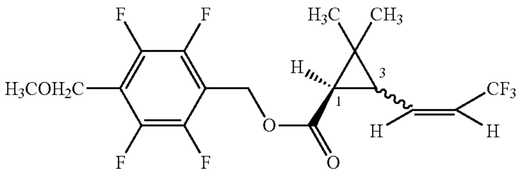

wherein the carbon-carbon double bond in carboxylic acid moiety is Z configuration, and the absolute stereo configuration at the 1-position of cyclopropane is R configuration, namely, the compound is 2,3,5,6-tetrafluoro-4-methoxymethylbenzyl-1R-(Z)-3-(3,3,3-trifluoro-1-propenyl)-2,2-dimethylcyclopropanecarboxylate, wherein the pesticide does not contain 2,3,5,6-tetrafluoro-4-methoxymethylbenzyl-1S-(Z)-3-(3,3,3-trifluoro-1-propenyl)-2,2-dimethylcyclopropane carboxylate.

2. The pesticide comprising a pyrethroid compound according to claim 1, characterized in that the stereostructure of three-membered ring of chrysanthemic acid moiety in the compound is trans-configuration, namely, the compound is 2,3,5,6-tetrafluoro-4-methoxymethylbenzyl-1R, trans-(Z)-3-(3,3,3-trifluoro-1-propenyl)-2,2-dimethylcyclopropanecarboxylate.

3. The pesticide comprising a pyrethroid compound according to claim 1, characterized in that the stereostructure of three-membered ring of chrysanthemic acid moiety in the compound is cis-configuration, namely, the compound is 2,3,5,6-tetrafluoro-4-methoxymethylbenzyl-1R, cis-(Z)-3-(3,3,3-trifluoro-1-propenyl)-2,2-dimethylcyclopropanecarboxylate.

4. A method of preparing the pyrethroid compound according to claim 1, characterized in that an esterification reaction between 1R-(Z)-3-(3,3,3-trifluoro-1-propenyl)-2,2-dimethylcyclopropanecarboxylic acid represented by formula (B)

(B)

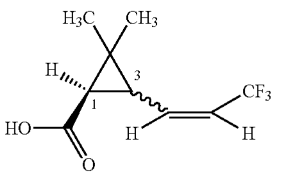

and 2,3,5,6-tetrafluoro-4-methoxymethylbenzyl alcohol is performed at a molar ratio of 0.8 to 1.2:1 in the presence of sulfuric acid or p-toluenesulfonic acid in an organic solvent at 60-130° C. to obtain the pyrethroid compound, wherein a molar ratio of catalyst sulfuric acid or p-toluenesulfonic acid to 2,3,5,6-tetrafluoro-4-methoxymethylbenzyl alcohol is 0.01 to 0.1:1.

5. A method of preparing the pyrethroid compound according to claim 1, characterized in that 1R-(Z)-3-(3,3,3-trifluoro-1-propenyl)-2,2-dimethylcyclopropane carboxylic acid represented by formula (B) is acyl chloridized by an acyl chloridizing reagent to obtain 1R-(Z)-3-(3,3,3-trifluoro-1-propenyl)-2,2-dimethylcyclopropane carboxylic acid chloride, followed by reacting with 2,3,5,6-tetrafluoro-4-methoxymethyl benzyl alcohol to obtain the pyrethroid compound.

6. The method according to claim 4, characterized in that the compound represented by formula (B) is obtained by isolating 1R-3-(3,3,3-trifluoro-1-propenyl)-2,2-dimethylcyclopropanecarboxylic acid by recrystallization, wherein a solvent used for recrystallization is methanol-water, a weight ratio of methanol to water is 0.1 to 10:1 and that of 1R-3-(3,3,3-trifluoro-1-propenyl)-2,2-dimethylcyclopropane carboxylic acid to the solvent used for recrystallization is 0.05 to 0.1:1.

7. The method according to claim 6, characterized in that said 1R-3-(3,3,3-trifluoro-1-propenyl)-2,2-dimethylcyclopropane carboxylic acid is obtained by reacting an aldehyde ester of formula (C)

(C)

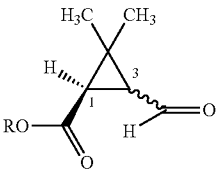

wherein R═$CH_3$,$CH_2CH_3$ with a wittig reagent $(C_6H_5)_3P^+$—$CH_2CF_3$— at a molar ratio of 0.8 to 1.2:1 in THF under 0-40° C. for 5-20 hours to form a compound of formula (D)

(D)

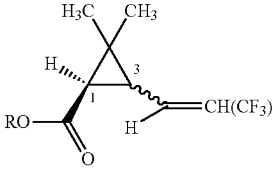

wherein R═$CH_3$,$CH_2CH_3$, followed by hydrolysis.

8. A method of controlling sanitary pests comprising exposing the pests to the pesticide according to claim 1.

9. The method according to claim 8, characterized in that said sanitary pests are mosquitoes, flies, or blattella germanicas.

10. The method according to claim 8, characterized in that a pesticide incense coil, electric heating mosquito-repellent mat, or electric heating liquid mosquito-repellent incense containing the compound according to claim 1 is prepared, and the compound is volatilizable under heating.

11. The method according to claim 5 characterized in that the compound represented by formula (B) is obtained by isolating 1R-3-(3,3,3-trifluoro-1-propenyl)-2,2-dimethylcyclopropanecarboxylic acid by recrystallization, wherein a solvent used for recrystallization is methanol-water, a weight ratio of methanol to water is 0.1 to 10:1 and that of 1R-3-(3,3,3-trifluoro-1-propenyl)-2,2-dimethylcyclopropane carboxylic acid to the solvent used for recrystallization is 0.05 to 0.1:1.

12. The method according to claim 11 characterized in that said 1R-3-(3,3,3-trifluoro-1-propenyl)-2,2-dimethylcyclopropane carboxylic acid is obtained by reacting an aldehyde ester of formula (C)

(C)

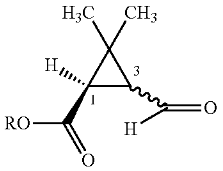

wherein R═$CH_3$,$CH_2CH_3$ with a wittig reagent $(C_6H_5)_3P^+$—$CH_2CF_3$— at a molar ratio of 0.8 to 1.2:1 in THF under 0-40° C. for 5-20 hours to form a compound of formula (D)

(D)

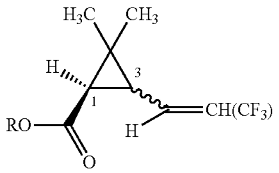

wherein R═$CH_3$,$CH_2CH_3$, followed by hydrolysis.

13. The method according to claim 8 wherein a ribbon-shaped paper containing the compound according to claim 1 is prepared, and the compound is volatilized at room temperature.

* * * * *